United States Patent [19]

Wilberg

[11] Patent Number: 4,775,372

[45] Date of Patent: Oct. 4, 1988

[54] DEVICE FOR APPLICATION OF LIQUIDS TO SURFACE OF HANDS

[76] Inventor: Janice L. Wilberg, 1274 N. State St. #1, Orem, Utah 84057

[21] Appl. No.: 30,580

[22] Filed: Mar. 27, 1987

[51] Int. Cl.⁴ .................. A61M 35/00; A61F 13/00
[52] U.S. Cl. ............................ 604/290; 604/292; 604/306; 401/6; 401/7
[58] Field of Search ............ 604/290, 292, 293, 289, 604/303, 304, 306; 2/159; 401/6, 8, 7; 128/114.1; 450/38

[56] References Cited

U.S. PATENT DOCUMENTS

| 880,041 | 2/1908 | Renton | 604/308 |
|---|---|---|---|
| 2,501,565 | 3/1950 | Halley | 401/7 X |
| 2,507,386 | 5/1950 | Spiegel | 604/289 X |
| 2,670,473 | 3/1954 | Stebic | 2/159 |
| 3,116,732 | 1/1964 | Cahill | 604/292 |
| 3,298,368 | 1/1967 | Charos | 604/292 X |
| 3,342,182 | 9/1967 | Charos | 604/292 |
| 3,384,083 | 5/1968 | Cozza et al. | 604/292 X |
| 3,896,807 | 7/1975 | Buchalter | 604/292 X |
| 4,117,841 | 10/1978 | Perrotta et al. | 604/306 X |
| 4,476,588 | 10/1984 | Long | 604/292 X |
| 4,567,065 | 1/1986 | Schneiderman | 604/292 X |
| 4,622,035 | 11/1986 | Palmer et al. | 604/289 X |

Primary Examiner—Richard J. Apley
Assistant Examiner—David J. Bender

[57] ABSTRACT

A device for application of liquids to the surface of hands which permits slow release of the liquid on the surface of the hands and at the same time permits one to continue to work with their hands. The device is shaped like a glove or mit prepared from a thin flexible sheet material possessing a plurality of spaced enclosed small pouches containing the liquid to be applied to the hands, the glove or mit also having a wrist band which fits tightly around the wrist to prevent the treatment liquid from running onto the wrist while the gloves are in place. The pouches are either punctured prior to placing the glove on the hand, or are burst by application of external pressure on the device after being placed on the hand.

10 Claims, 1 Drawing Sheet

DEVICE FOR APPLICATION OF LIQUIDS TO SURFACE OF HANDS

BACKGROUND OF THE INVENTION

1. Field of the Invention

This invention relates to a new device for the application of liquids to the surface of human hands. More particularly, the invention relates to a new type of gloves adapted to the application of liquids, such as oils and lotions, to the surface of hands.

Specifically, the invention relates to a new type of glove adapted to the application of liquids to the hand surfaces which permits slow release of the liquid on the surface of the hands and at the same time permits one to continue to work with their hands while the treatment with the liquid is taking place. The new device broadly comprises a glove or mit prepared from a thin flexible sheet material possessing a plurality of spaced enclosed small pouches containing the liquid to be applied to the hands, said glove or mit also having a wrist band which fits tightly around the wrist to prevent the treatment liquid from running onto the wrist while the gloves are in place.

The invention further provides a method for utilizing the new device for the treatment of the hand surfaces which broadly comprises placing the above-described gloves or mit on the hand and then by applying pressure to the top side of the pouches forcing the liquid out of the pouch onto the surface of the hand, the location and number of pouches to be opened by the pressure depending on the area of the hand to be treated and the desired length of treatment.

2. Prior Art

It is well known that the surface of the hands often become dry and irritated from constant exposure to air, water, soap, etc. and sometimes rashes appear due to changes in diet, exposure to plants and bushes, etc. To relieve this type of irritation, one often applies oils, lotions, medicated creams and the like by rubbing such materials directly on the surfaces of the hand. Only small amounts of such material may be added, however, or the excess would run off the hands and cause quite a mess wherever the hands were place. Such a small addition generally only gives momentary relief, and it is necessary to constantly apply the solution to the hands. This constant application takes considerable time and greatly limits the use of the hands for other purposes. In addition, the type of work to be done while the material is on the hands is limited as it is necessary to avoid touching things which might be damaged by the treating material.

It is an object of the invention, therefore, to provide a new device for the application of liquids to the surfacts of human hands. It is a further object to provide a new device for applying liquids to the surface of hands which permit one to maintain the application for extended periods of time. It is a further object to provide a device for applying liquids to the surface of hands which eliminates the problem of run off of any excess liquid added. It is a further object to provide a device for applying liquids to the surface of the hands which permits one to continue to use the hands for work assignments while the application is continuing. It is a further object to provide a method for applying liquids to hands which eliminates the danger of having the liquid rub off and cause damage to material in contact therewith. These and other objects of the invention will be apparent from the following detailed description thereof.

SUMMARY OF THE INVENTION

It has now been discovered that these and other objects may be accomplished by the new device for the application of liquids to hands of the present invention which provides for the first time an easy and efficient way to apply liquids to hands to correct the above-noted problems.

The new device of the present invention broadly comprises a glove or mit prepared from a thin flexible sheet material possessing a plurality of spaced enclosed small pouches containing the liquid to be applied to the hands, said gloves or mits also having a wrist band which fits tightly around the wrist to prevent the treatment liquid from running onto the wrist while the gloves are in place.

The new device of the present invention is utilized to accomplish the intended purpose by placing the above-noted new gloves or mits on the hand or hands to be treated and then applying pressure to the top side of the pouches forcing the liquid out of the pouch onto the surface of the hand, the location and number of pouches to be opened by the pressure depends on the area of the hand to be treated and the desired length of treatment.

It has been surprisingly found that by the use of the new gloves or mits by the method described above one can apply a great variety of different liquid materials to the surface of hands over an extended period of time. Thus, by breaking only a limited number of the pouches over a period of time the treatment can continue for long periods. Even when most of the pouches are broken, the presence of the glove tends to keep the liquid in contact with the skin far longer than if applied by conventional method of rubbing the liquid on the skin of the hand. Further advantage is found in the fact that the gloves retain the liquid on the surface of the skin and permits one to continue working with the hands for conventional tasks without having to stop to add more liquid or to wipe away the dripping liquid from the wrist and arm. In addition, the presence of the gloves to retain the liquid prevents the liquid from doing damage to sensitive material in which the hand may come it contact. Many of the liquids to be applied, and particularly those having medicinal purposes may be irritating to the eyes or other parts of the face or body, and with the present invention such possibilities can be avoided as the liquids and fumes therefrom are clearly retained within the gloved area.

DESCRIPTION OF THE DRAWING

The various objects and features of the present invention will be more fully understood by reference to the accompanying drawing.

With reference to FIG. 1, the plastic glove is shown as 10, with the pouches illustrated by 11 and the wrist band as 12.

With reference to FIG. 2, the glove 11 is placed over finger 16 with the liquid shown inside the pouch as 13.

With reference to FIG. 3, which is side view of the preferred material to be used in preparing the new device of the present invention, a thin film of plastic is shown as 15, the pouch as 11 with the enclosed liquid as 13 and the protective film of plastic over the top of the pouch as 14.

DETAILED DESCRIPTION OF THE INVENTION

Figure 1:
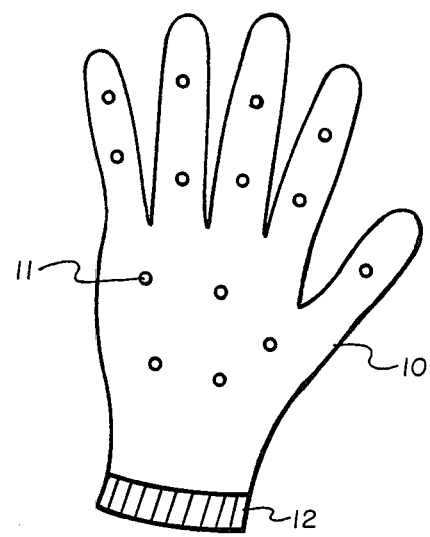
FIG. 1 is a top view of the glove showing the presence of the pouches.
Figure 2:
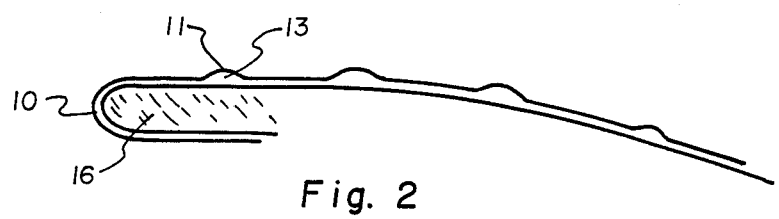
FIG. 2 is a side view of one of the fingers showing the side view of the pouches.
Figure 3:
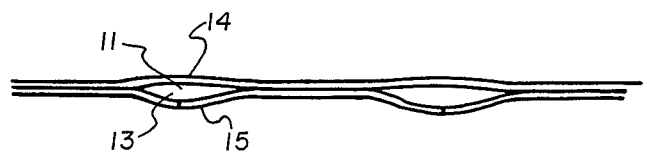
FIG. 3 is a schematic drawing showing an embodiment wherein the glove material is formed by placing the liquid in a depression on one sheet of plastic and another sheet is placed thereover.

While the above-described description of the invention and drawing have been made in rather specific terms, it should be understood that various changes can be made in construction and operation without departing from the scope of the invention.

It should be noted that while the drawing shows the device as being a glove with the five finger sections, the device could very well be just a mit with no fingers showing or only one or two of the finger sections protruding from the mit.

The size of the pouches on the glove or mit may vary over a wide range depending chiefly on the liquids to be used and the intended use of the gloves or mit. In most cases, the pouches will vary in size from about 1/16 to ⅜ inches in diameter, but preferably from about ⅛ to ½ inches in diameter.

The location and spacing of the pouches on the glove or mit may vary over a wide range depending chiefly on the intended use thereof and the techniques of manufacture. In general, the pouches may be spaced from about ½ inch to about 3 inches apart or even wider distances if desired. The pouches generally are placed all over the surface of the glove so as to cover the top and bottom of the hand as well as the top and bottom of the finger area. Preferably, however, the pouches are placed only on the top of the hand and on the palm of the hand as the liquids coming out of such pouches generally find their way to the finger area. In addition, the general irriation to be treated is generally on the top of the hand or on the palm so those are the areas generally desired to be treated.

The liquid in the pouch or bubble may be any type of liquid which is suitable for treatment of the problems that have developed or might develop on the skin of the hand. This includes, among others, almond oil, Jojoba oil, Vitamin E oil, olive oil, oils and lotions containing aloe vera and Swiss herbs, sun tan lotion, and the like and mixtures thereof. In most cases, the preferred liquids to be used are the fluid to viscous oils and lotions which have some medicinal purpose in the treatment of the skin.

The glove itself is made of thin flexible sheet material which may be of any composition as long as it meets the above requirements. Preferred material include the thin sheet of plastic, and particularly those of thicknesses varying from about 1/32 to ⅛ inches and are of the thermoplastic type. Examples of such materials include sheets of polypropylene, polyethylene, polycarbonates, polyvinyl chloride and the like. Preferably the sheet material is colorless so that the pouches may be more easily seen, although colored sheets may be used if desirable.

Any desired method may be used in the manufacture of the gloves as long as the desired liquid can be placed in the proper number of pouches. A preferred method of manufacture includes forming a large sheet of heat deformable plastic of about 1/16 inches in width. The proper number of open pouches are then formed by pressing the end of a hot rod against the sheet in the proper places to form the pouch of about ⅛ to ¼ inches in depth. The suitable techniques. A thin sheet of the same or different thermoplastic material is then placed over the top of the sheet containing the liquid and heated so as to effect a proper bond between the two sheets of plastic. The glove can then be formed from the plastic sheet as prepared above by conventional glove forming apparatus.

Other less preferred method includes forming the glove with the pouches empty and then introducing the liquid through hypodermic needles into each of the pouches.

The wrist band attached to the glove may be of any desirable type as long as it is expandible and fits tightly around the wrist of the user. Such bands can be made from flexible plastic, woven material, etc. and is preferably about 1 to 3 inches in width and goes completely around the end of the glove. The wrist band can be added during or after the manufacture of the glove as described above.

The new gloves of the present invention may be used in any suitable manner depending on the type and structure of the glove. If the glove is prepared from very thin plastic sheeting, the pouches may be broken when desired by merely pressing hard on top surface of the pouch. If the glove is prepared from thicker sheeting material, it may be desirable to turn the glove inside out and prick each of the pouches inner sides with a very thin pin or needle so as to form an opening of extremely thin diameter, such as 1/64 to 1/32 inches. As most liquids are very viscous, they will come out of the pouch through that opening only when pressure is applied on the top surface of the pouch as noted above.

As some liquid treatments of the hand are best done with warm or hot liquids, it is sometimes desirable to put the glove in warm or hot water before applying to the hand, or after the glove has been placed on the hands.

As the gloves are of little value after the pouches have been emptied, they may be discarded or if desired effort may be made to introduce more liquid into the pouches by use of the hypodermic needle as noted above.

PREFERRED EMBODIMENT OF THE INVENTION

A preferred embodiment of the invention is described below. It should be understood, however, that this is given as a preferred assembly of the glove for illustration purposes only and is not to be regarded as limiting the invention in any way.

A thin sheet of polypropylene of about 1/32 inches in thickness was spread out and small pouches about 1½ inches apart and about ⅜ inches deep were prepared by pressing hot rod agains the polypropylene sheet. Almond oil was then placed in each of the pouches so formed to the level of the top of the sheet. A thin sheet of the same polypropylene was then layed over the top and heat applied so as to effect a bond between the two sheets. For some cases, addition of an adhesive helped effect the proper bonding.

A glove was then formed from the above sheet using conventional glove forming apparatus. After the glove was formed a 2 inch wide highly flexible rubber band was adhered to the end of the glove so as to permit the glove to fit tightly against the wrist of the user.

After the glove was formed, it was turned inside out and a very thin needle was used to puncher the pouches and the glove placed on the left hand of the user. The right hand was then used to press firmly on the outside of the pouches and force the almond oil onto the surface of the hand. The oil slowly was forced out of the pouch over a period of time and and the user was able to continue to use the hand without any danger of dripping on the hand or having to reapply the oil to the surface of the hand.

I claim as my Invention:

1. A device for application of liquids to the surface of human hands which permits slow release of the liquid on the said surfaces consisting essentially of a glove or mit for a human hand prepared from a thin flexible plastic sheet material possessing a plurality of spaced enclosed pouches containing the liquid to be applied to the hands, said pouches to be punctured prior to use, or burst by application of external pressure on the device after being placed on the hand, said pouches being spaced such that they come in contact with at least the top of the hand and fingers and palm of the hand, said glove or mit also having a wrist band which fits tightly around the wrist of the user, and said glove having no layers in the glove other than the said plastic sheet.

2. A device as in claim 1 wherein the pouches are placed from about 1 inch to 3 inches apart on the glove surface.

3. A device as in claim 1 wherein the pouches are a from about $\frac{1}{8}$ to $\frac{3}{8}$ inches in depth.

4. A device as in claim 1 wherein the liquid in the pouches is almond oil.

5. A device as in claim 1 wherein the liquid is JoJoba oil.

6. A device as in claim 1 wherein the liquid in the pouches is an aloe vera oil.

7. A device as in claim 1 wherein the inside bottom of a plurality of the pouches has been pierced to form an opening for the liquid to be pressed onto the surface of the hand.

8. A device as in claim 1 wherein the thin flexible sheet material is a thin polypropylene sheet.

9. A device as in claim 1 wherein the thin flexible sheet material is a rubber sheet material.

10. A process for treatment of hand surfaces while still having the hands free for other work which comprises placing the gloves as defined inclaim 1 on the hands and then applying pressure to the outside of the pouches to effect a release of the enclosed liquid onto surface of the hands.

* * * * *